US00PP37068P2

(12) United States Plant Patent
Molnar et al.

(10) Patent No.: US PP37,068 P2
(45) Date of Patent: Oct. 28, 2025

(54) ***CORNUS* PLANT NAMED 'Rutstar'**

(50) Latin Name: *Cornus elwinortonii*
Varietal Denomination: Rutstar

(71) Applicant: Rutgers, The State University of New Jersey, Piscataway, NJ (US)

(72) Inventors: Thomas J. Molnar, East Brunswick, NJ (US); John M. Capik, Allenhurst, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 19/038,066

(22) Filed: Jan. 27, 2025

(51) Int. Cl.
*A01H 6/00* (2018.01)
*A01H 5/00* (2018.01)

(52) U.S. Cl.
USPC ..... Plt./220
CPC ..... *A01H 6/00* (2018.05)

(58) Field of Classification Search
USPC ..... Plt./216, 220
See application file for complete search history.

(56) References Cited

PUBLICATIONS

Rutgers University Office for Research. 2025. Intellectual property of Dogwood 'Starlight'. https://research.rutgers.edu/agricultural-products/dogwoods/starlight#tab=panel-3. 1 page.*

* cited by examiner

*Primary Examiner* — Karen M Redden
(74) *Attorney, Agent, or Firm* — Daugherty & Del Zoppo, LPA; Patrick J. Daugherty

(57) ABSTRACT

A new Cornus cultivar of interspecific hybrid origin, *Cornus elwinortonii* (*Cornus kousa* x *Cornus nuttallii*), that is clearly distinguished by its floriferous display of large, bright-white floral bracts, attractive dark-green foliage, and tolerance of the incitants of powdery mildew.

4 Drawing Sheets

Latin name of genus and species of the plant claimed: *Cornus elwinortonii.*
Variety denomination: 'Rutstar'.

BACKGROUND OF THE INVENTION

This new cultivar is the product of a long-standing program of hybridization and selection of big-bracted dogwoods, in this instance the result of an open-pollination event of an unnamed white-bracted *Cornus elwinortonii* (*Cornus kousa* x *Cornus nuttallii*) interspecific hybrid tree held in a germplasm collection located in East Brunswick, New Jersey. The purpose of the program is to develop new and superior cultivars of dogwoods expressing attractive, white-colored floral bracts that are large in size and cold hardy in New Jersey and similar climates. The seed parent of this new cultivar is a white-bracted, unreleased breeding selection designated as KN161-1. KN161-1 resulted from the germination of an open-pollinated seed of the unreleased breeding selection KN30-1, which originated from the cross of the unreleased breeding selection KN3 x *C. kousa* 'Rosea'. KN3 was derived from a cross of *C. kousa* 'Chinensis' x *C. nuttallii* 'Goldspot' made by Dr. Elwin Orton in 1973. The staminate (pollen) parent of 'Rutstar' is unknown. However, since dogwoods are self-incompatible and insect pollinated, the male parent is expected to be one of the dogwood trees in a dedicated block of unreleased breeding selections planted in an isolated area at in East Brunswick, New Jersey, specifically for cross pollination purposes. The progeny from which 'Rutstar' was selected were planted in a field in East Brunswick, New Jersey, in 2009 and evaluated for their phenotypic differences and assessed for value as commercial cultivars.

The inventors selected a specific seedling tree hereof from a dedicated set of progeny trees grown in a cultivated area, and as a result, have in turn caused the same to be asexually reproduced by budding and grafting. The asexual reproduction and growth and selection of the new cultivar took place in the vicinity of East Brunswick, New Jersey. The claimed cultivar is stable and reproducible true-to-type in successive generations of asexual reproduction.

As will be demonstrated from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore stated.

BRIEF SUMMARY OF THE INVENTION

The cultivar, designated here as 'Rutstar', originated in a cultivated field at a horticultural farm located at 67 Ryders Lane, East Brunswick, Middlesex County, New Jersey, 08816. Its specific location was row 12 in the H3D field of said horticultural farm and was evaluated under the identification code RUT 20-50. This seedling originated from an open-pollination event in 2008 of a *Cornus elwinortonii* (*Cornus kousa* x *Cornus nuttallii*) tree designated KN161-1 as part of a cross-pollination breeding block of unnamed dogwood selections located in Hillsborough Township, New Jersey.

The seedling, which became this new cultivar, germinated in February 2009, was transplanted to progressively larger containers, and was finally transplanted to the field in September 2009 at said horticulture farm in East Brunswick, New Jersey. The cultivar was evaluated in place for its ornamental attributes and performance. After four years of floral bloom (2013-2016), it was first asexually propagated by budding onto *C. kousa* seedling rootstock in August 2016 in Belvidere, Tennessee, and in Boring, Oregon, and was subsequently evaluated in those regions for propagation performance, powdery mildew response, growth habit and leaf quality, and floral bract characteristics. Five budded trees were returned to said horticultural farm in East Brunswick, New Jersey, in March 2018 from Belvidere, Tennessee, grown in containers until September and then field planted at said horticultural farm in East Brunswick, New Jersey for observation along with the original seedling.

The Cornus (dogwood) tree of the present invention may be asexually propagated by grafting (usually chip-budding), by softwood cuttings, or via meristem culture (plant tissue culture). It is distinguished from patented and/or commercially available cultivars of *C. elwinortonii* (*C. kousa* × *C. nuttallii*), *C. rutgersensis* (*C. florida* x *C. kousa*) hybrids, and pure species *C. kousa* in the following respects:

*Cornus elwinortonii*:

'KN30-8', U.S. Plant Pat. No. 16,309, Venus® has larger floral bracts than 'Rutstar', specifically the average involucral bract spread (n=25 measurements) measured at East Brunswick, New Jersey, for 'KN30-8' was 17.9 cm (upper) and 16.2 cm (lower) compared to 16.2 cm (upper) and 15.5 cm (lower) for 'Rutstar'. Further, they differ in floral bract shape. Individual floral bracts of 'KN30-8' are globose in shape, apiculate at their tip, and attenuate at their base, whereas 'Rutstar' individual floral bracts are ovate in shape, acuminate at their tip, and obtuse to rounded at their base. Further, flower anthesis and peak of bloom display in New Jersey of 'KN30-8' is 10-14 days prior to anthesis of 'Rutstar', which occurs around May 25 to June 1.

'KN4-43', U.S. Plant Pat. No. 16,293, Starlight®, has a smaller floral bract spread than 'Rutstar'. More particularly, the measured floral bract spread of 'KN4-43' (n=25 measurements) is 11.9 cm (upper) and 10.9 cm (lower), compared to 16.2 cm (upper) and 15.5 cm (lower) for 'Rutstar'. 'KN4-43' also has notably smaller flower stalk peduncles compared to 'Rutstar', with a size of 2.1 cm (n=10) for 'KN4-43' compared to a size of 11.3 cm (n=25) for 'Rutstar'. Furthermore, flower anthesis and peak bloom display in New Jersey of 'KN4-43' is similar to 'KN30-8', with both being 10-14 days prior to anthesis of 'Rutstar'.

'KN144-2', U.S. Plant Pat. No. 26,211 P3,, Rosy Teacups® differs from 'Rutstar' in its pink-colored floral bracts; the floral bracts of 'Rutstar' are white with no shades of pink other than a minor amount that occasionally can appear at the floral bract margins. Also, the upward growth and development of 'KN144-2' young floral bracts, which continues to the point of anthesis giving them a "cup-like" character, are unlike those of 'Rutstar' which are similar to the floral bract development of the straight species *C. kousa*.

*Cornus rutgersensis*:

The *C. rutgersensis* cultivars are discussed collectively as they have similar characteristics that can be easily differentiated from 'Rutstar', the most apparent being bloom phenology, specifically true flower anthesis, which corresponds to peak floral display. For example, 'Rutcan', U.S. Plant Pat. No. 7,210 (Constellation®); 'Rutban', U.S. Plant Pat. No. 7,205 (Aurora®); 'Rutlan', U.S. Plant Pat. No. 7,732 (Ruth Ellen®), 'Rutgan', U.S. Plant Pat. No. 7,207 (Stellar Pink®); and 'KF1-1', U.S. Plant Pat. No. 17,768 (Saturn®) can be clearly differentiated from 'Rutstar' as their true flower anthesis is 2-3 weeks earlier in the season in New Jersey, around the date of May 15, which is intermediate between bloom dates of their respective parents *C. florida* and *C. kousa*. 'Rutstar' blooms at the general time of *C. kousa* in New Jersey, which occurs around May 25 to June 5 in East Brunswick, New Jersey. Furthermore, the floral bract shapes of the *C. rutgersensis* cultivars listed are all much more rounded (globose) in shape at their tips, more like *C. florida*, whereas the floral bracts of 'Rutstar' are ovate and acuminate/pointed at their tips, more similar in their structure to those of *C. kousa*. The *C. rutgersensis* cultivars listed are also all sterile, producing no mature fruits containing seeds (Mattera et al., 2015), whereas 'Rutstar' produces abundant fruit resembling those of *C. kousa*, with fertile seeds.

'KF111-1', U.S. Plant Pat. No. 22,219, Hyperion® blooms closer to the date of 'Rutstar' and overlaps in some years. However, it has a smaller floral bract spread than 'Rutstar': 'KF111-1' measured (n=25 measurements) 12.9 cm (upper) and 11.3 cm (lower). The floral bracts of 'KF111-1' are also globose in shape, unlike 'Rutstar' with ovate floral bracts. Also, 'KF111-1' has shorter floral bract peduncles with an average length of 6.3 cm (n=10) compared to 11.3 cm (n=25) for 'Rutstar'.

*Cornus kousa*:

In general, 'Rutstar' has a larger involcural bract spread than the straight species *C. kousa* cultivars available in the nursery trade, including seedlings and asexually propagated cultivars. Seven cultivars were measured in comparison to 'Rutstar' in an evaluation trial located at East Brunswick, NJ (n=25 flower heads for 'Rutstar' and n=10 for the comparison cultivars). 'Rutstar' had an average involucral bract spread of 16.2 cm (upper) and 15.5 cm (lower). This is compared to 1) 'Greensleeves', not patented, averaged 13.1 cm (upper) and 12.6 cm (lower); 2) 'China Girl', not patented, averaged 9.6 cm (upper) and 9.2 cm (lower); 3) 'Galzam', Galilean®, not patented, averaged 13.4 cm (upper) and 12.2 cm (lower); 4) 'MADI-II', U.S. Plant Pat. No. 26,653, Mandarin Jewel® averaged 9.9 cm (upper) and 9.0 cm (lower); 5) 'Madison', U.S. Plant Pat. No. 16,129 P2, Crown Jewel™ averaged 11.8 cm (upper) and 10.10 cm (lower); 6) 'Snow Tower', not patented averaged 14.3 cm (upper) and 13.4 cm (lower); and 7) 'Blue Shadow', not patented, averaged 11.0 cm (upper) and 10.5 cm (lower).

'Pam's Mountain Bouquet' (U.S. Plant Pat. No. 25,575 P3) also has smaller floral bracts as defined its US plant patent description as an average spread of 7.4 cm but can also be differentiated from 'Rutstar' by the nature of its fused floral bracts. Over 80% of the individual floral bracts of 'Pam's Mountain Bouquet' can exhibit a form of fusion, whereas they are not separated at their bases like the typical form of *C. kousa*. 'Rutstar' has fully separated bracts and fusion has not been observed.

A group of seven pink-bracted *C. kousa* cultivars available in the nursery trade includes 'Rutpink' (Scarlet Fire® U.S. Plant Pat. No. 28,311 P3), 'Satomi' (not patented, also called 'Miss Satomi'), 'Rosabella' (not patented), 'Rosea' (not patented), 'Schmred' (Heart Throb®, U.S. Plant Pat. No. 9,283 P), 'Hanros' (not patented, Radiant Rose®), Beni Fuji (U.S. Plant Pat. No. 8,676 P), which are easily differentiated from 'Rutstar' which has bright white floral bracts.

'Rutstar' has solid-colored leaves lacking variegation, thus is easily distinguished from variegated *C. kousa* such as 'Samzan' Samaritan™ (not patented), 'Summer Fun' (not patented), 'Wolfeyes' (not patented), Tri-splendor (U.S. Plant Pat. No. 20,008 P2), and 'Summer Gold' (not patented).

'Rutstar' is associated with the trademark Stellar Nova™. Further discussion of the Latin name is found at Mattera R., Molnar T., Struwe L. (2015) "*Cornus* x *elwinortonii* and *Cornus* x *rutgersensis* (Cornaceae), new names for two artificially produced hybrids of big-bracted dogwoods." PhytoKeys 55:93-111.

BRIEF DESCRIPTION OF THE DRAWINGS

This new cultivar of dogwood is illustrated by the accompanying digital images that capture defining characteristics of the tree at the age of seven (7) years by the best possible color representation using digital color photography. All color references below are measured against The Royal Horticultural Society (RHS) Colour Chart (1966). Colors are approximate as individual color depends on horticultural practices such as light level, temperature, and fertilization rate, among others.

DETAILED BOTANICAL DESCRIPTION

Figure 1:
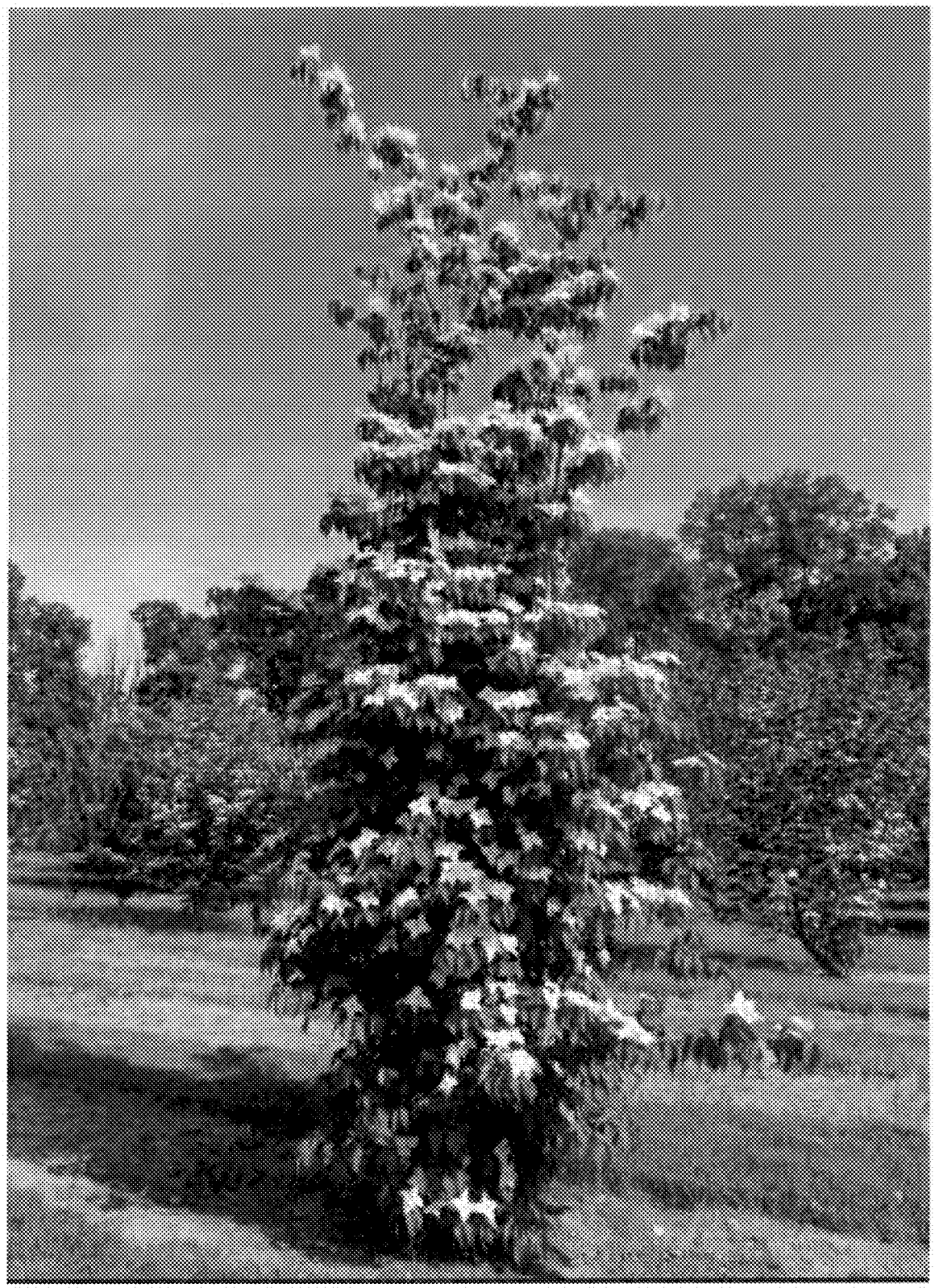
FIG. 1 shows image of the original tree of 'Rutstar' at peak floral display after seven growing seasons from germination showing its vigorous, upright growth habit. Picture taken May 29, 2016.
Figure 2:
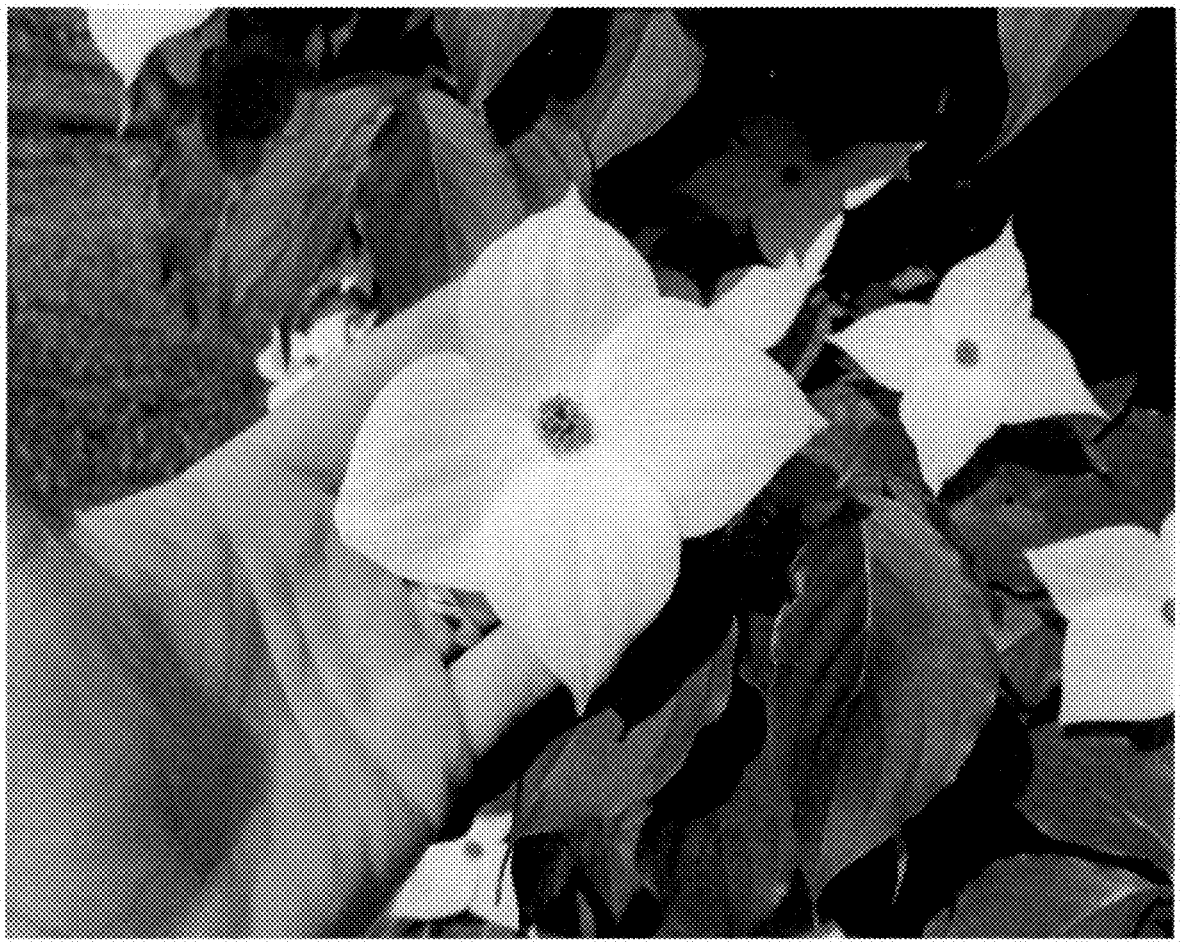
FIG. 2 shows a close-up view of a characteristic individual 'Rutstar' flower head at peak ornamental display. Note that the image shows the ovate floral bracts with acuminate tip and overlapped bases.
Figure 3:
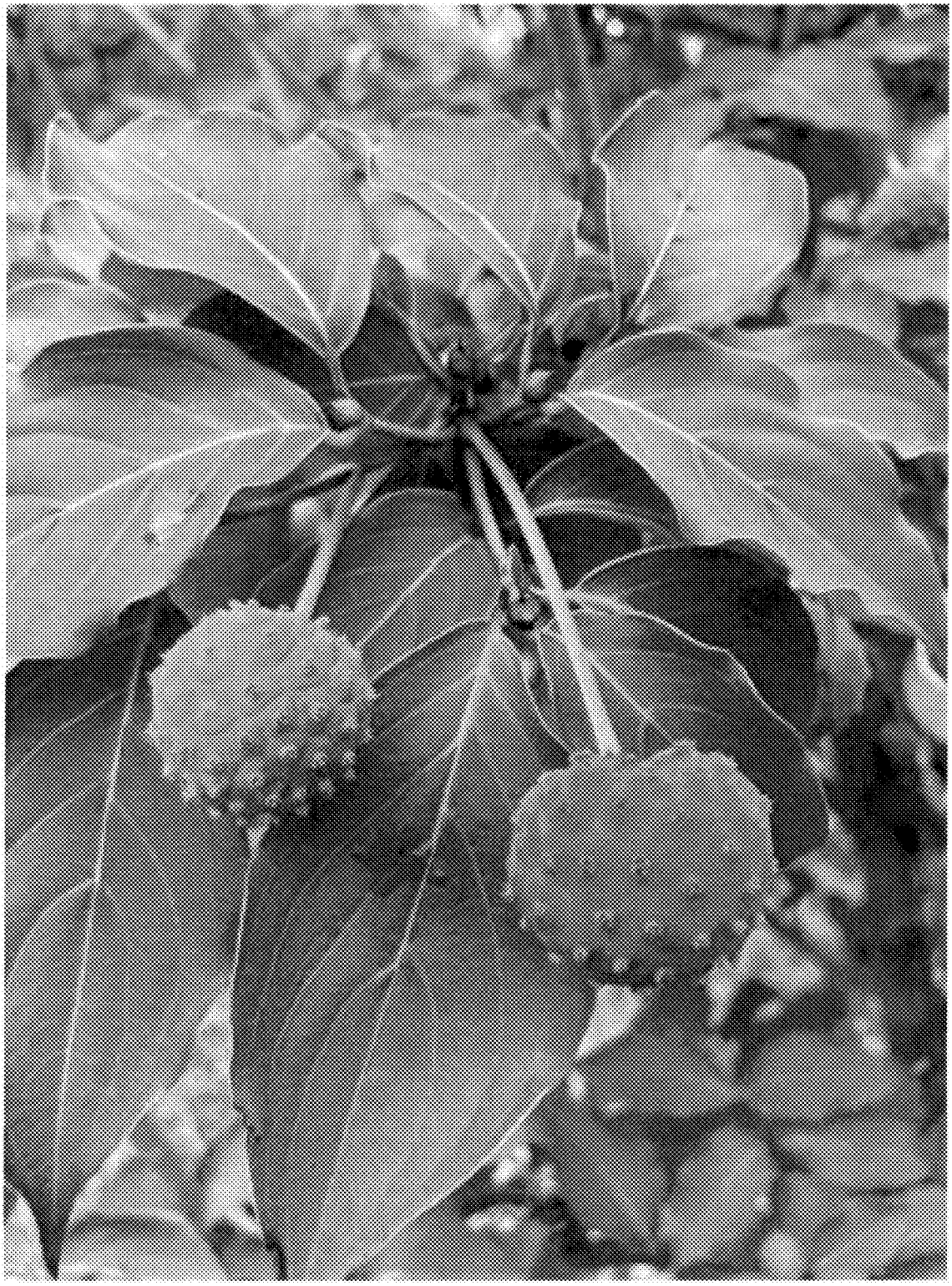
FIG. 3 shows the color and shape of mature fruit of 'Rutstar', which is similar in appearance to the species *Cornus kousa*.
Figure 4:
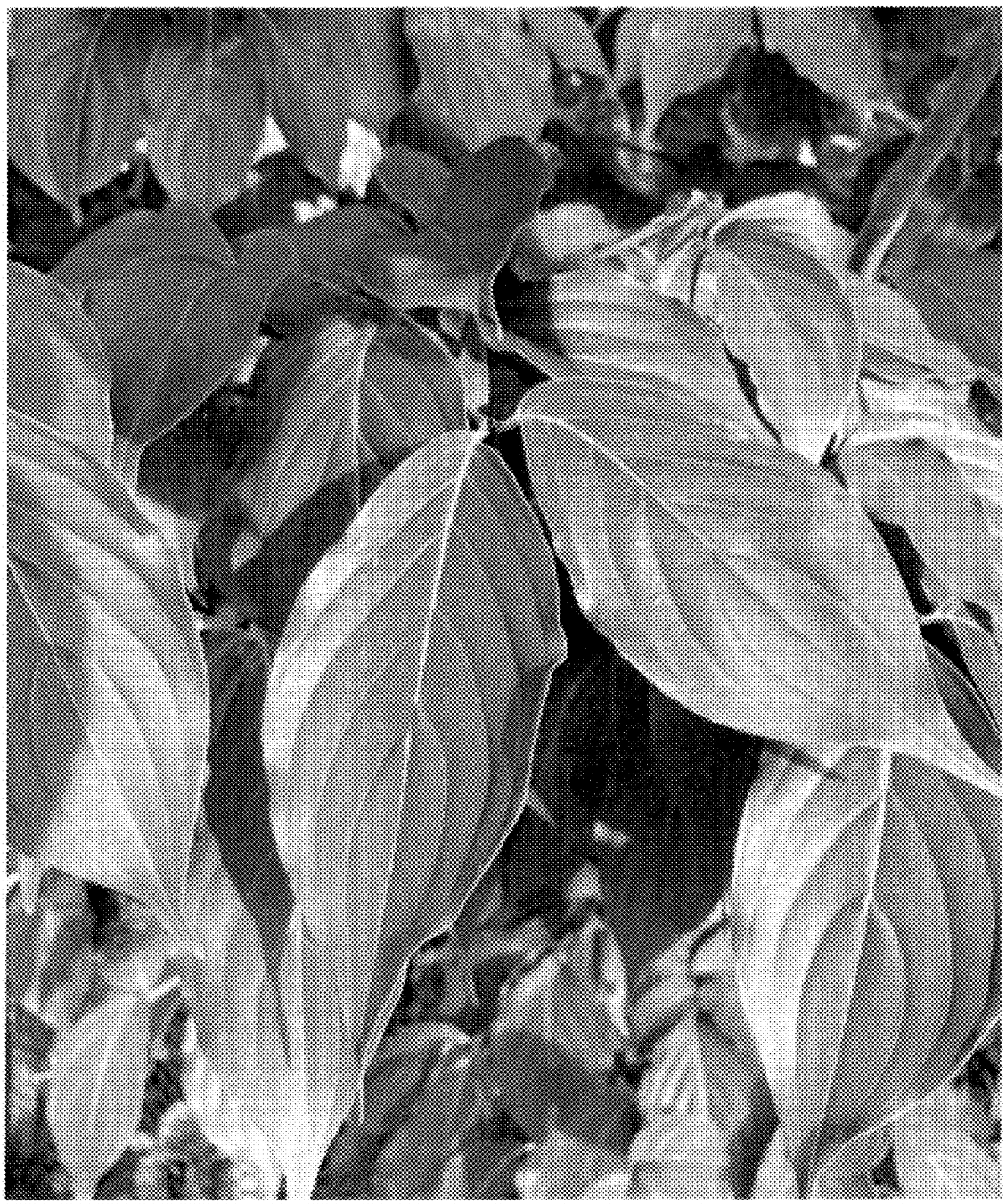
FIG. 4 shows the leaf shape and color of 'Rutstar' including its entire margin with only occasional, minor undulations on the leaf margin.

*Form*.—Tree. Growth habit: Dense tree branched low to ground with prominent upright branches which form a rounded head at maturity. Vigorous, approximately three times taller than wide as a young tree and then maturing to two times taller than wide as branches spread.

*Height*.—4.0 meters at 7 years. Spread: 1.5 meters at 7 years. Plant vigor is greater than *Cornus kousa* species and more similar to *C. rutgersensis* hybrid dogwoods.

*Cold hardiness*.—The original seedling tree planted in 2009 and all grafted propagules thereof (n=25 to date, since 2018 planting) have suffered no visible winter injury to vegetative or floral buds during the winters under test in the field at East Brunswick, New Jersey, in USDA Plant Hardiness Map Zone 7b (0 to 5 degrees Fahrenheit).

*Resistance to insects and diseases*.—No evidence of insect problems has been observed on the original seedling or its propagules in the years the plants have been under test in the states of New Jersey, Tennessee, and Oregon. No sign or symptom of powdery mildew has been observed. No evidence of susceptibility to dogwood anthracnose or common dogwood borer has been presented.

*Trunk*.—Circumference of the trunk at 10 cm above the soil level was 35 cm after seven growing seasons. Texture: Smooth, although some parts sandpaper rough due to presence of lenticels.

*Color of bark on trunk and main scaffold branches*.—Closest to 197A and 197B Greyed Green Group. Younger stems (1 and 2 years) closest to 200 B and 200 C Brown Group. Three-year-old branches closest to 197B and 197C Greyed Green Group and slightly textured due presence of lenticels (average 10-15 per cm2). Lenticels are closest in color to 197 D Greyed Green Group. Size of lenticels are 1.0-2.0 mm long by 0.3 mm-0.4 mm wide. Lenticels are present on younger stems but are less than 1.0 mm long, same color.

*Branches*.—Crotch angle 35-45 degrees for large, major branches, but 45-70 degrees for subsequent smaller branches.

Foliage:

*Leaf arrangement*.—Opposite. Leaf size: Lamina. Average length: 12.6 cm (range 10.0 to 15.4 cm; n=25). Average width: 6.6 cm (5.5 to 7.9 cm; n=25), the widest point being a little more than half-way down from the tip. Petiole: Average length 9.6 mm (range 6-12 mm, n=25).

*Shape*.—Ovate/elliptic. Tip: Acuminate. Base: Rounded. Number of pairs of veins: 5 to 6. Margin: mostly entire but some very slightly wavy (undulate) depending on growing conditions.

*Texture*.—Adaxial surface is smooth. The abaxial surface is slightly fuzzy due to tiny trichomes on the blade and tufts of longer, thin hairs in clumps along the midrib and the secondary veins, especially at the junctures of the midvein and 4th and 5th pairs of secondary veins.

*Coloration*.—Solid.

*Mature leaf color*.—Adaxial: Closest to 137 A B Green Group with midrib and other veins from petiole to tip 144 B and C Yellow Green Group. Abaxial: Closest to 138 B Green Group. The color of the mid vein on the abaxial side and secondary veins are 145 C Yellow Green group.

Fall leaf color (October to November), East Brunswick, New Jersey. Adaxial surface: Leave primarily 137A Green Group but mottled with colors 187A Greyed-Purple Groups, 183A Greyed-Purple Group, 53A Red Group, 46A Red Group, and 43A Red Group). Abaxial surface: 138A Green Group. Leaf color is dependent on environmental factors such as soil type, sun exposure, temperature, day length, available water and nutrients. Thus, leaf color may vary from one area to another and year.

*Inflorescence*.—Location where observations were made: East Brunswick, New Jersey. Type of inflorescence: Flower head. Dense, rounded mound. Peduncle size (late May at time of anthesis): Average length (n =25): 11.3 cm (range=9.0 cm to 15.6 cm). Average width (n =25): 1.8 mm (range=1.5 cm-2.0 cm).

*Floral Bracts*.—Number: Four (two opposing pairs, lower and upper).

'Rutstar' individual lower and upper floral bracts are similar in size and shape, with the lower bracts being just slightly larger on average. The average width of the lower bracts is consistently slightly larger than the upper bract. Bract length and width will vary slightly from year-to-year based on environmental conditions and flower head numbers within the tree canopy, but the relationship between the size of the upper and lower bracts and the ratio of length to width across all bracts remains consistent.

The following floral bract dimensions were determined at a floral period in East Brunswick, New Jersey from late May to early June, where "n" equals the number of respective measurements. Lower floral bract dimensions: average length 7.92 cm, n=50; average width 5.38 cm, n=50; and Involucral spread 16.22 cm, n=25. Upper floral bract dimensions: average length 7.82 cm, n=50; average width 5.22 cm, n=50; and Involucral spread 15.5 cm, n=25.

*Shape*.—The individual floral bracts are primarily ovate, acuminate at their tip, and obtuse to rounded at their base. For most flower heads, bracts overlap their adjacent partner bract at their bases close to 20% of their total width at anthesis. Younger bracts show no overlap.

*Color*.—At peak of floral display (approximately May 28 to June 5 in East Brunswick, New Jersey) in full sun exposure: Adaxial: Ranges between 158 C and 158 D Yellow White Group, most being 158 C. Occasionally, a trace of 51A Red Group is present at the floral bract margins and tip. Abaxial: Closest to 158 D Yellow White Group. Peduncle of flower head at peak floral display is 145 A Yellow Green group.

*Flower description*.—Very floriferous. Single flowers arranged in compact, dense heads subtended by the large floral bracts. The average number of true flowers per flower head is 50, ranging from 35 to 55 (n=20). No observed fragrance. Flowers are not persistent. Floral display of the involucral bracts typically lasts about four weeks depending on weather conditions.

*Flowering habit*.—Anthesis of the tiny, relatively inconspicuous true flowers generally begins around the time of peak ornamental display of the floral bracts (approximately May 28 to June 5 in East Brunswick, New Jersey).

*Petals*.—Four petals per true flower each of similar dimensions. Oblong in shape with rounded tips that reflex away from the stigma at time of anthesis. Length approximately 2.0 mm (n=4). Width approximately 1.0 mm (n=4). Color similar on upper and lower surfaces: 144 C Yellow-Green Group. All figures are based on an average of the 4 measurements.

Reproductive Organs:

*Stamens per flower*.—4.

*Filament*.—Length: approximately 2.5 mm (n=4). Width: approximately 0.3 mm (n=4). Color: 155B White Group.

*Anther*.—Length: approximately 0.4 mm (n=4). Width: approximately 0.8 mm (n=4). Color: 162A Greyed-Yellow Group.

*Pollen*.—Color of freshly dehisced pollen is approximately 158 A Yellow White Group.

*Style*.—Height: approximately 1.5 mm (n=4). Width: approximately 0.2 mm (n=4). Color: 144 C Yellow-Green Group.

*Stigma*.—Height: approximately 0.25 mm (n=4). Width: approximately 0.5 mm (n=4). Color: 144 C Yellow-Green Group. All figures are based on an average of the 4 measurements.

Fruit:

Flower head with mature fruit. Fruits are 2-celled, typically 1-seeded, fleshy drupes that form a mounded, raspberry-like syncarp averaging 27.7 mm in length, 26.5 mm in width, and 23.0 mm in height (n =20). The many ovaries are enclosed in a fleshy, rounded mass typical for fruit of *Cornus kousa*. The exterior of the aggregate fruit is smooth except for the dried floral parts at the tip of each individual drupe (the dried remains of the sepals and the persistent style and stigma).

Fruit color varies from green to yellow to orange to pink as the fruit matures and finally to 46A to 42C Red Group. Fruits ripen in September and can persist for around 6 weeks.

*Seed*.—Color when dry: Closest to 165 C to 165 D Greyed Orange Group. Size: Average 7.0 mm length, 5.0 mm width, and 4.0 mm in thickness (n=20). Shape: typical for *Cornus kousa*. Average number of seeds per fruit is 15 (n =20).

What is claimed is:

1. A new and distinct cultivar dogwood tree named 'Rutstar', substantially as herein shown and described.

* * * * *